United States Patent
Dijk et al.

(10) Patent No.: US 9,377,387 B2
(45) Date of Patent: Jun. 28, 2016

(54) METHOD AND MEASURING SYSTEM FOR ASCERTAINING DENSITY OF A FLUID

(71) Applicant: Endress + Hauser Flowtec AG, Reinach (CH)

(72) Inventors: Coen Van Dijk, Biel-Benken (DE);
Omar Momente, Liestal (CH);
Heinerich Hagenmeyer,
Grenzach-Wyhlen (DE)

(73) Assignee: Endress + Hauser Flowtec AG, Reinach (CH)

( * ) Notice: Subject to any disclaimer, the term of this patent is extended or adjusted under 35 U.S.C. 154(b) by 403 days.

(21) Appl. No.: 13/716,637

(22) Filed: Dec. 17, 2012

(65) Prior Publication Data

US 2014/0060154 A1    Mar. 6, 2014

(30) Foreign Application Priority Data

Dec. 23, 2011 (DE) .......................... 10 2011 089 808

(51) Int. Cl.
*G01N 9/00* (2006.01)
*G01F 1/84* (2006.01)
*G01F 1/74* (2006.01)

(52) U.S. Cl.
CPC .............. *G01N 9/002* (2013.01); *G01F 1/8436* (2013.01); *G01F 1/8477* (2013.01); *G01F 1/74* (2013.01); *G01F 1/8413* (2013.01); *G01N 2009/006* (2013.01)

(58) Field of Classification Search
CPC ............ G01N 9/002; G01N 2009/006; G01N 29/022; G01N 29/036; G01F 1/8477; G01F 1/8436
USPC .................................................. 73/649, 32 A
See application file for complete search history.

(56) References Cited

U.S. PATENT DOCUMENTS 4,763,530 A     8/1988  Mizerak
4,876,879 A *  10/1989  Ruesch ..................... G01F 1/74
                                                                73/32 A (Continued)

FOREIGN PATENT DOCUMENTS

CN          87106872 A      6/1988
CN         101523165 A      9/2009

(Continued)

OTHER PUBLICATIONS

International Search Report, EPO, The Netherlands, Apr. 2, 2013.

(Continued)

*Primary Examiner* — Hezron E Williams
*Assistant Examiner* — Truong Phan
(74) *Attorney, Agent, or Firm* — Bacon & Thomas, PLLC

(57) ABSTRACT

A method for producing at least one oscillation measurement signal, which has vibrations of a vibratory body are registered. A temperature sensor is applied thermally attached with a non fluid contacting, second surface of the vibratory body for producing a temperature measurement signal representing a time curve of a variable temperature of the vibratory body. The temperature measurement signal can follow, however time delayed, a change of the temperature of the vibratory body from a beginning temperature value, to a new temperature value. Based on the oscillation measurement signal as well as the temperature measurement signal, density, measured values are produced representing the density, wherein, during such, discrepancies possibly occurring between the time curve of the temperature of the vibratory body and the temperature measurement signal are taken into consideration, respectively at least partially compensated.

21 Claims, 8 Drawing Sheets

(56) References Cited

U.S. PATENT DOCUMENTS

| | | | |
|---|---|---|---|
| 5,687,100 A * | 11/1997 | Buttler | G01F 1/8413 702/100 |
| 6,845,663 B2 | 1/2005 | Lopatin | |
| 8,165,828 B2 | 4/2012 | Tombs | |
| 8,229,695 B2 | 7/2012 | Pruysen | |
| 2005/0044929 A1 * | 3/2005 | Gysling | G01F 1/74 73/32 A |
| 2005/0072238 A1 * | 4/2005 | Wenger et al. | 73/649 |
| 2007/0017278 A1 * | 1/2007 | Francisco | G01F 1/8409 73/32 A |
| 2008/0115577 A1 * | 5/2008 | Headrick | 73/32 A |
| 2009/0312977 A1 * | 12/2009 | Pruysen | G01F 1/8413 702/100 |
| 2011/0167910 A1 * | 7/2011 | Storm | G01F 1/74 73/32 A |
| 2011/0219872 A1 | 9/2011 | Hussain | |
| 2011/0224940 A1 | 9/2011 | Howe | |
| 2011/0271756 A1 * | 11/2011 | Lalla | G01F 1/8422 73/32 A |
| 2014/0060154 A1 | 3/2014 | Dijk | |

FOREIGN PATENT DOCUMENTS

| | | |
|---|---|---|
| DE | 3744325 A1 | 7/1988 |
| DE | 10257322 A1 | 5/2004 |
| DE | 102006054007 A1 | 5/2008 |
| EP | 2795287 | 10/2014 |
| WO | 2004053428 A2 | 6/2004 |
| WO | 2007095547 A2 | 8/2007 |
| WO | 2013092104 A1 | 6/2013 |

OTHER PUBLICATIONS

German Search Report, The German Patent Office, Munich, Aug. 3, 2012.

English Translation of IPR, WIPO, Geneva, Jul. 3, 2014.

* cited by examiner

METHOD AND MEASURING SYSTEM FOR ASCERTAINING DENSITY OF A FLUID

TECHNICAL FIELD

The invention relates to a method for ascertaining density, ρ, of a fluid contacting an oscillatably held, vibratory body, which can be excited to execute vibrations. The invention relates as well as to a corresponding measuring system suitable for performing the method.

BACKGROUND DISCUSSION

Used often in industrial process measurements technology for ascertaining density of fluid flowing in a pipeline or stored in a container are measuring systems, in the case of which an oscillatably held, vibratory body, as part of a physical to electrical, measuring transducer, is brought into contact with the fluid to be measured, namely with a volume portion thereof. The vibratory body—contacted by fluid—is caused during operation to vibrate in such a manner, for example, actively by means of an electro-mechanical oscillation exciter acting on the vibratory body, that the vibratory body executes, at least partially, resonant oscillations, namely mechanical oscillations with a resonant frequency, which is dependent on the mechanical construction of the vibratory body, as well as also on the density of the fluid. The measuring transducer is, for such purpose, most often applied in a container wall of the container, for example, a tank, holding the fluid or in the course of a line, for example, a pipeline, through which the fluid is moving, and is equipped also to register vibrations of the vibratory body and to produce at least one oscillation measurement signal, which has at least one signal component with a signal frequency corresponding to the resonant frequency and, consequently, dependent on the density of the fluid. Examples of such measuring transducers, respectively measuring systems, formed by means of one or more vibratory bodies and thus suitable for measuring density, are described in, among others, EP-A 564 682, EP-A 919 793, US-A 2007/0028663, US-A 2008/0127745, US-A 2010/0083752, US-A 2010/0236323, US-A 2011/0219872, U.S. Pat. No. 4,524,610, U.S. Pat. No. 4,801,897, U.S. Pat. No. 5,027,662, U.S. Pat. No. 5,054,326, U.S. Pat. No. 5,796,011, U.S. Pat. No. 5,965,824, U.S. Pat. No. 6,073,495, U.S. Pat. No. 6,138,507, U.S. Pat. No. 6,148,665, U.S. Pat. No. 6,044,694, U.S. Pat. No. 6,389,891, U.S. Pat. No. 6,651,513, U.S. Pat. No. 6,688,176, U.S. Pat. No. 6,711,942, U.S. Pat. No. 6,845,663, U.S. Pat. No. 6,912,904, U.S. Pat. No. 6,938,475, U.S. Pat. No. 7,040,179, U.S. Pat. No. 7,102,528, U.S. Pat. No. 7,272,525, U.S. Pat. No. 7,549,319, U.S. Pat. No. 7,681,445, U.S. Pat. No. 7,874,199, WO-A 00/19175, WO-A 01/02816, WO-A 01/29519, WO-A 88/02853, WO-A 93/01473, WO-A 93/19348, WO-A 93/21505, WO-A 94121999, WO-A 95/03528, WO-A 95/16897, WO-A 95/29385 or WO-A 98/02725. In accordance therewith, the vibratory body can be e.g. a measuring tube inserted into the course of the line carrying the fluid, thus a measuring tube through which the fluid is flowing—for instance, the measuring tube of a measuring transducer of a measuring system in the form of a purely density measuring device for flowing fluids, in the form of a Coriolis, mass flow/-density measuring device and/or in the form of a density-/viscosity measuring device—or, however, e.g. also a vibratory body formed by means of an oscillating cylinder extending into the fluid—located in a line or in a container—and formed, in given cases, in rod—or paddle shape and/or internally hollow, consequently provided e.g. also by a vibronic fill level limit switch measuring also density, supplementally to a limit of fill-level.

The measuring transducer is, furthermore, connected with an electronics of the measuring system serving for evaluation of the at least one oscillation measurement signal and for generating corresponding density, measured values representing the density. In the case of modern measuring systems of the type being discussed, such electronics are, as described in, among others, also in U.S. Pat. No. B 6,311,136 or U.S. Pat. No. A 6,073,495, most often implemented by means of one or more microprocessors formed, in given cases, also as digital signal processors (DSP). Besides evaluation of the at least one oscillation measurement signal delivered by the measuring transducer and representing oscillations of its vibratory body, the electronics serves also to generate at least one driver signal, for example, an harmonic and/or clocked, driver signal, for an electro-mechanical oscillation exciter acting on the vibratory body and serving for actively exciting said oscillations, for example, an electro-mechanical oscillation exciter having an exciter coil interacting with a permanent magnet affixed on the vibratory body or a piezoelement affixed on the vibratory body, wherein the driver signal has a signal component with a signal frequency matched to the resonant frequency of the vibratory body. The signal component, respectively the driver signal, can, for example, also be controlled as regards its electrical current level and/or voltage level.

In the case of measuring systems of the type being discussed, the electronics is most often accommodated within at least one, comparatively robust, especially impact-, pressure-, and/or weather resistant, electronics housing. The electronics housing can be arranged, for example, remotely from the measuring transducer and connected therewith only via a flexible cable; it can, however, also be arranged, as shown e.g. also in the initially mentioned U.S. Pat. No. 5,796,011, directly on the measuring transducer or on a measuring transducer housing separately housing the measuring transducer, and thus, also, its vibratory body. Moreover, however, as shown in, among others, WO-A 01/29519, it is also quite usual, in given cases, to use modularly formed electronics accommodated in two or more separate housing modules for forming measuring systems of the type being discussed.

In the case of measuring systems of the type being discussed, the electronics is usually electrically connected via corresponding electrical lines to a superordinated electronic data processing system most often arranged spatially removed from the respective device. Most often, the electronic data processing system is also spatially distributed. Measured values produced by the respective measuring system are forwarded near in time by means of a measured value signal correspondingly carrying the measured values. Measuring systems of the type being discussed are additionally usually connected with one another by means of a data transmission network provided within the superordinated data processing system and/or with corresponding electronic process controls, for example, on-site programmable logic controllers or process control computers installed in a remote control room, where the measured values produced by means of the respective measuring system and digitized and correspondingly coded in suitable manner are forwarded. By means of such process control computers, the transmitted measured values can be further processed and visualized as corresponding measurement results e.g. on monitors and/or converted into control signals for other field devices embodied as actuating devices, such as e.g. magnetically operated valves, electric-motors, etc. Since modern measuring arrangements can most often also be monitored and, in given cases, controlled and/or configured directly from such control computers, operating data intended for the measuring system are equally dispatched in corresponding manner via the aforementioned data transmission networks, which are most often hybrid as regards the transmission physics and/or the transmission logic. Accordingly, the data processing system serves usually also, to condition the measured value signal delivered by the measuring system in accordance with the requirements of downstream data transmission networks, for example, suitably to digitize the measured value signal and, in given cases, to convert such into a corresponding telegram, and/or to evaluate such on-site. For this purpose, there are provided in the data processing systems, electrically coupled with the respective connecting lines, evaluating circuits, which pre- and/or further-process as well as, in case required, suitably convert, the measured values received from the respective measuring system. Serving for data transmission in such industrial data processing systems are at least sectional, especially serial, fieldbusses, such as e.g., FOUNDATION FIELDBUS, RACKBUS-RS 485, PROFIBUS, etc., or, for example, also networks based on the ETHERNET standard, as well as the corresponding, most often comprehensively standardized, transmission protocols. Alternatively or supplementally, in the case of modern measuring systems of the type being discussed, measured values can also be transmitted wirelessly per radio to the respective data processing system.

Besides the evaluating circuits required for processing and converting the measured values delivered from the respectively connected measuring system, such superordinated data processing systems have most often also electrical supply circuits serving for supplying the connected measuring— and/or switching devices with electrical energy. Such electrical supply circuits provide a supply voltage for the respective electronics and drive the electrical currents flowing through electrical lines connected thereto as well as through the respective electronics. In given cases, such voltage is fed directly from the connected fieldbus. A supply circuit can, in such case, be associated with, for example, exactly one measuring system, respectively a corresponding electronics, and can be accommodated, together with the evaluating circuit associated with the respective measuring system—, for example, united into a corresponding fieldbus adapter—in a shared electronics housing, e.g. in the form of a hatrail module. It is, however, also quite usual to accommodate supply circuits and evaluating circuits, in each case, in separate electronics housings, in given cases, spatially remote from one another and to wire them together via external lines.

In the case of measuring systems for density measurement, wherein the measuring system operates by means of a vibratory body, such as disclosed in, among others, the initially mentioned WO-A 88/02853, WO-A 98/02725, WO-A 94/21999, in the case of ascertaining the density $\rho$ based on the resonant oscillations of the vibratory body, or its resonant frequency $f_r$, the temperature $\theta_{10}$ of the vibratory body, thus a temperature of the vibratory body dependent on a temperature of the fluid to be measured, consequently a variable temperature of the vibratory body, is to be take into consideration. For ascertaining such, a local temperature $\theta_{sens}$ of the vibratory body on a surface of the vibratory body facing away from the fluid, consequently a "dry" surface not contacted thereby, is registered by sensor, usually by means of a thereon adhered, platinum resistor of a resistance thermometer or by means of a thermocouple adhered on said surface, as well as a corresponding measuring circuit in the electronics. Such temperature is then correspondingly taken into consideration in ascertaining the density, for instance, according to the relationships, $\theta_{sens}\sim\theta_{10}$, $f_r^2=f(\theta_{sens}\to\theta_{10})$, or $f_r^2=f(1/\rho)$. An additional improvement of the accuracy, with which the density can ultimately be measured, can be achieved in the case of measuring systems of the type being discussed, not least of all in the case of such having as vibratory body a measuring tube clamped on its two ends, in among other ways, by registering, as mentioned, among others, also in US-A 2011/0219872, furthermore, mechanical deformations of the vibratory body located in its static rest position, for instance, deformations as a result of a changing temperature of the vibratory body and/or as a result of forces acting on the vibratory body, or mechanical stresses within the vibratory body resulting therefrom and correspondingly taking such into consideration in calculating the density. Such mechanical deformations of the vibratory body can be registered, for example, by means of one or more strain sensors mechanically coupled with the vibratory body via its "dry" surface.

Further investigations on measuring systems of the type being discussed have, however, shown that, based on the measured temperature $\theta_{10}$ and resonant frequency $f_r$, the density $\rho$ of fluids can indeed be very exactly ascertained, namely directly with a relative measuring error of less than 0.2%, in cases where temperature remains constant over longer periods of time of several minutes or more. However, especially in the case of a change of the fluid in the line, the density measured for the "new" fluid can, first of all, deviate considerably from its actual density; this—even in the case of application of strain sensors—unluckily, at times, even in such a manner that, in the case of a fluid with a density actually reduced relative to the preceding fluid, first of all, a higher density than earlier is ascertained, respectively also, conversely, in spite of greater density for the "new" fluid, first of all, a lesser density is ascertained. Consequently, the measuring error for the density has, in comparison to its change, an opposite sign, respectively, the measuring system has, insofar, an all-pass characteristic.

SUMMARY OF THE INVENTION

Taking this into consideration, it is an object of the invention to provide a method for ascertaining density of a fluid by means of a vibratory body contacted thereby, which method is successful also directly after said fluid is introduced into the vibratory body as replacement for another fluid. The method should work as much as possible while using conventional vibratory bodies, respectively, while using conventional sensor arrangements serving for registering the temperature of the vibratory body.

For achieving the object, the invention resides in a method for ascertaining density of a fluid contacting an oscillatably held, vibratory body excitable to execute vibrations, for example, a vibratory body of metal, wherein the vibratory body has a specific thermal conductivity of, for example, greater than 5 W K$^{-1}$ m$^{-1}$, thus a thereon dependent, thermal conductance effective for heat transfer from, on the one hand, a fluid contacting, first surface of the vibratory body, which has a fluid temperature, namely a temperature of the fluid contacting the first surface, to, on the other hand, a non fluid contacting, second surface, as well as having a heat capacity, and wherein a temperature of the vibratory body, namely a temperature of the vibratory body dependent on the fluid temperature, is variable. The method comprises steps of causing the vibratory body contacted by fluid to vibrate in such a manner that it executes, at least partially, resonant oscillations, namely mechanical oscillations with a resonant frequency dependent on the density of the fluid contacting the first surface of the vibratory body as well as also on the temperature of the vibratory body, as well as registering vibrations of the vibratory body for producing at least one oscillation measurement signal, which has at least one signal component with a signal frequency corresponding to the resonant frequency and consequently dependent on the density of the fluid, applying a temperature sensor thermally coupled with the vibratory body via its second surface for producing a temperature measurement signal representing a time curve of a temperature of the vibratory body, namely a temperature of the vibratory body dependent on a temperature of the fluid contacting the vibratory body on its first surface, wherein the temperature measurement signal, not least of all as a result of the thermal conductance and the heat capacity of the vibratory body, follows a change of the temperature of the vibratory body from a beginning first temperature value to a second temperature value only time delayed, a change resulting, for example, from a change of the temperature of the fluid contacting the vibratory body on its first surface and/or from a fluid change, so that the temperature measurement signal corresponds consequently to said second temperature value only time delayed. Furthermore, the method of the invention comprises a step of producing a measured value of density based on the oscillation measurement signal as well as the temperature measurement signal during a change of the temperature of the vibratory body resulting, for example, from a change of the temperature of the vibratory body on its first surface. Indeed, the measured value of density is produced in such a manner that a discrepancy, especially a time dependent discrepancy, occurring during the producing of the measured value of density between the time curve of the temperature of the vibratory body and the temperature measurement signal, is taken into consideration, for example, even at least partially compensated.

Furthermore, the invention resides in a measuring system for ascertaining density of a fluid, for example, a fluid flowing in a pipeline, which measuring system comprises a measuring transducer having at least one vibratory body, for example, a vibratory body of metal, which is oscillatably held and adapted to be contacted on a first surface by fluid to be measured in such a manner that the first surface assumes a fluid temperature, namely a temperature of the fluid contacting the first surface, and to be caused to vibrate in such a manner that it executes, at least partially, resonant oscillations, namely mechanical oscillations with a resonant frequency dependent on the density of the fluid, and which has a specific thermal conductivity, $\lambda_{10}$, for example, of greater than 5 W K$^{-1}$ m$^{-1}$, consequently a therefrom dependent, effective thermal conductance, $\Lambda_{10}$, for heat transfer from the first surface to a non fluid contacting, second surface, and a heat capacity, $C_{10}$, and having at least one oscillation sensor for registering vibrations of the measuring tube and for producing an oscillation measurement signal, which has at least one signal component with a signal frequency dependent on the density of the fluid, and having a temperature sensor thermally coupled with the second surface of the vibratory body for registering a temperature on the second surface of the vibratory body dependent on the fluid temperature, and for producing a temperature measurement signal representing a time curve of a temperature of the vibratory body, namely a temperature of the vibratory body dependent on the fluid temperature, wherein the temperature measurement signal, not least of all caused through the thermal conductance, $\Lambda_{10}$, and the heat capacity, $C_{10}$, of the vibratory body, follows a change of the temperature of the vibratory body from a beginning first temperature value to a second temperature value, only time delayed, for instance, a change of the temperature resulting from a change of the temperature of the fluid contacting the vibratory body on its first surface and/or a change of the fluid, so that the temperature measurement signal corresponds consequently to said second temperature value, only time delayed. The measuring system further comprises an electronics electrically connected with the measuring transducer for processing the oscillation measurement signal and the temperature measurement signal as well as for generating, based on both the oscillation—as well as also the temperature measurement signal, a measured value of density representing the density of the fluid. The electronics of the measuring system of the invention is, furthermore, arranged, during the generating of the measured value of density, to take into consideration a discrepancy occurring between the time curve of the temperature of the vibratory body and the temperature measurement signal, especially a time dependent discrepancy, especially in such a manner that said discrepancy is at least partially compensated.

According to a first embodiment of the method of the invention, such further comprises a step of applying the oscillation measurement signal for producing a measured value of frequency representing the resonant frequency of the vibratory body contacted by the fluid. Furthermore, the method comprises a step of applying the temperature measurement signal for producing a measured value of temperature representing the temperature of the vibratory body as well as a step of applying both the measured value of frequency as well as also the measured value of temperature for producing a measured value of density representing the density.

According to a second embodiment of the method of the invention, such further comprises a step of producing a sampled sequence of frequency, namely a sequence of digital frequency values ascertained at different points in time based on the at least one oscillation measurement signal. Such sequence approximates a time curve of the resonant frequency of the vibratory body. Developing this embodiment of the invention further, it is additionally provided that the sampled sequence of frequency is applied for producing a delayed sampled sequence of frequency, namely a sequence of digital frequency values ascertained at different points in time based on the sampled sequence of frequency, in order to approximate the time curve of the resonant frequency of the vibratory body, in such a manner that said delayed sampled sequence of frequency more slowly approaches a time curve of the resonant frequency following on a change of the resonant frequency, for example, a jump-like change of the resonant frequency, than the sampled sequence of frequency.

According to a third embodiment of the method of the invention, such further comprises a step of producing a sampling sequence of surface temperature, namely a sequence of digital temperature values ascertained at different points in time based on the at least one temperature measurement signal, in order to approximate a time curve of the temperature on the second surface of the vibratory body.

According to a fourth embodiment of the method of the invention, such further comprises a step of producing an estimated sequence of temperature of the vibratory body, namely a sequence of digital temperature values ascertained at different points in time based on the at least one temperature measurement signal, in order to approximate a time curve of the temperature of the vibratory body, in such a manner that said estimated sequence of temperature of the vibratory body more quickly approaches a time curve of the temperature of the vibratory body following on a change of the temperature on the second surface of the vibratory body, for example, a jump-like change and/or a change resulting from a change of the fluid temperature, than the temperature measurement signal.

According to a fifth embodiment of the method of the invention, such further comprises a step of applying a strain sensor mechanically coupled with the vibratory body via its second surface for producing a deformation measurement signal representing a time curve of a deformation of the vibratory body, namely a deformation of the vibratory body dependent on the temperature of the vibratory body and/or a force acting on such. Developing this embodiment of the invention further, it is, furthermore, provided to produce, and to apply for producing the measured value of density, a sampling sequence of deformation, namely a sequence of digital deformation measurement values ascertained at different points in time based on the at least one deformation measurement signal, in order to approximate a time curve of the deformation of the vibratory body.

According to a sixth embodiment of the invention, it is, furthermore, provided that the vibratory body is an oscillatably held measuring tube having a lumen surrounded by a tube, or pipe, wall, especially a wall of metal. Developing this embodiment of the invention further, the measuring tube is, furthermore, adapted to be immersed in fluid in such a manner that the first surface of the vibratory body contacting the fluid is formed by an outer surface of the tube, or pipe, wall and the non fluid contacting, second surface of the vibratory body by an inner surface of the tube, or pipe, wall facing the lumen. Alternatively thereto, the measuring tube can, however, also be adapted to carry fluid, for example, flowing fluid, wherein the first surface of the vibratory body contacting the fluid is formed by an inner surface of the tube, or pipe, wall facing the lumen and the non fluid contacting, second surface of the vibratory body by an outer surface of the tube, or pipe, wall.

According to a seventh embodiment of the invention, the vibratory body is adapted to convey fluid, respectively to have fluid flowing through it.

According to an eighth embodiment of the invention, the vibratory body is adapted to be immersed in fluid, or to be flowed on by fluid. Developing this embodiment of the invention further, it is, furthermore, provided that the vibratory body has an oscillatably held membrane, and that the first surface of the vibratory body contacting the fluid is formed by means of a first membrane surface and the non fluid contacting, second surface by a second membrane surface lying opposite the first membrane surface. In the case of this embodiment of the invention, the vibratory body can further have, for example, also a paddle affixed on the first membrane surface, thus a paddle protruding into the fluid.

A basic idea of the invention is at least partially to compensate previously unrecognized, dynamic measuring errors inherent in measuring systems of the type being discussed, errors such as can occur during a transition time period transient as regards the temperature of the vibratory body and resulting, for instance, from a fluid change and/or from a significant change of the fluid temperature. Such compensation is achieved by corresponding correcting of the measured resonant frequency and/or the temperature measured on the vibratory body, namely by subsequent conforming of the time curve of the measured resonant frequency to the time curve of the measured temperature regularly trailing relative to the measured resonant frequency, or by subsequent conforming of the time curve of the measured temperature to the time curve of the measured resonant frequency leading relative to the measured temperature.

BRIEF DESCRIPTION OF THE DRAWINGS

The invention as well as other advantageous embodiments thereof will now be explained in greater detail based on examples of embodiments presented in the figures of the drawing. Equal parts are provided in all figures with equal reference characters; when perspicuity requires or it otherwise appears sensible, already mentioned reference characters are omitted in subsequent figures. Other advantageous embodiments or further developments, especially also combinations of first only individually explained aspects of the invention, will become evident, furthermore, from the figures of the drawing, as well as also from the dependent claims per se. The figures of the drawing show as follows:

DETAILED DISCUSSION IN CONJUNCTION WITH THE DRAWINGS

Figure 1:
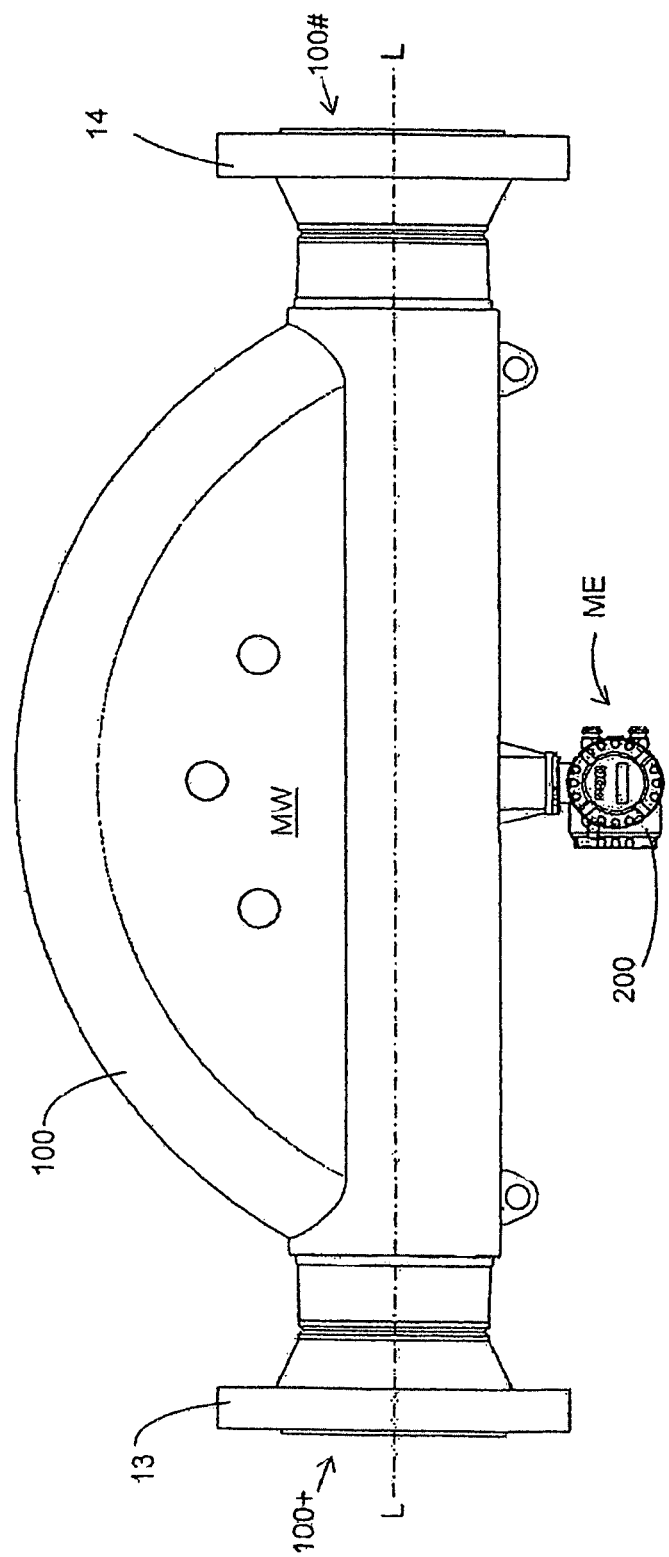
FIGS. 1, and 2 shows a measuring system (here embodied in the form of a compact measuring device) of industrial measuring—and automation technology for measuring density of a fluid flowing in a pipeline.
Figure 2:
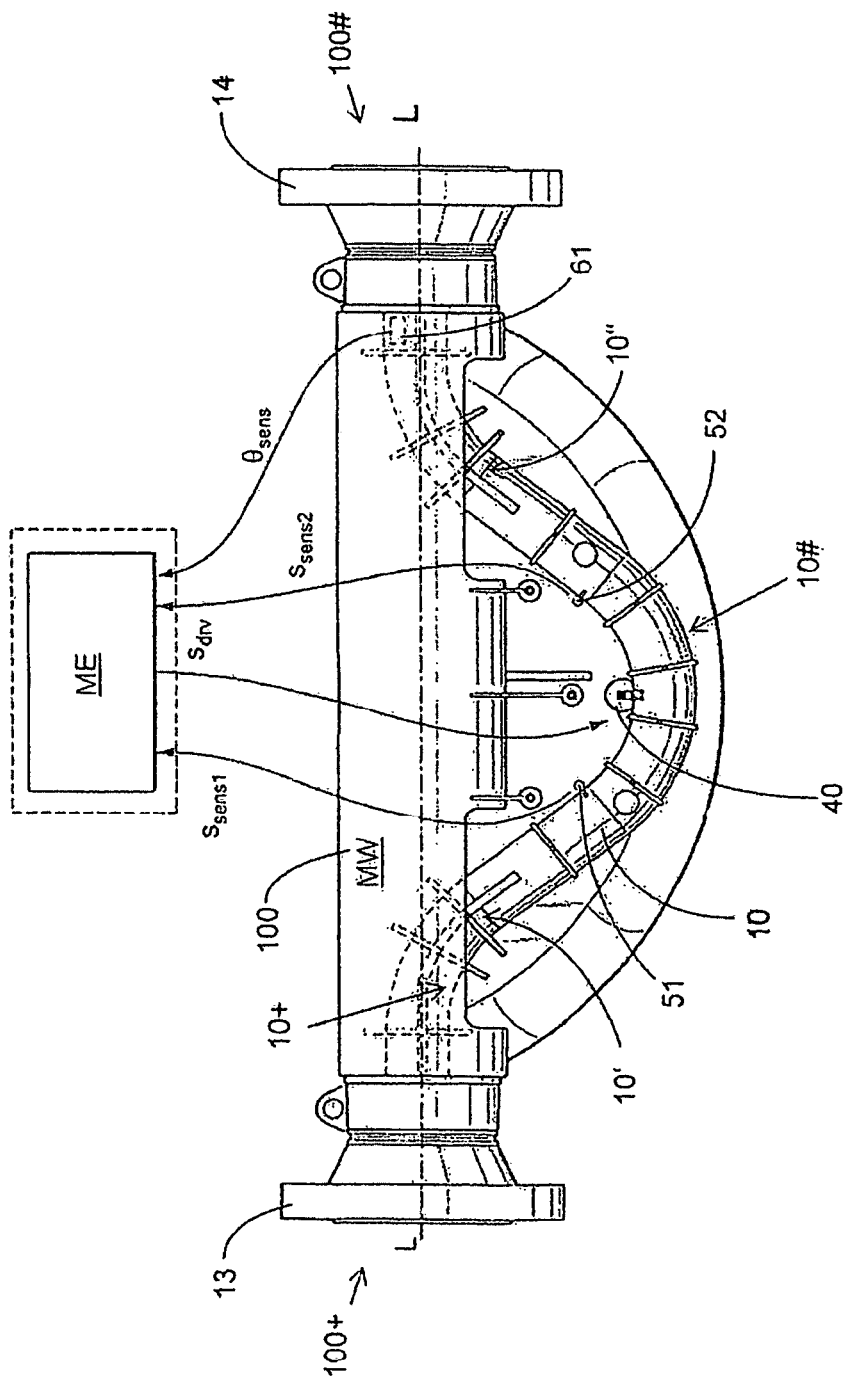
Figure 3:
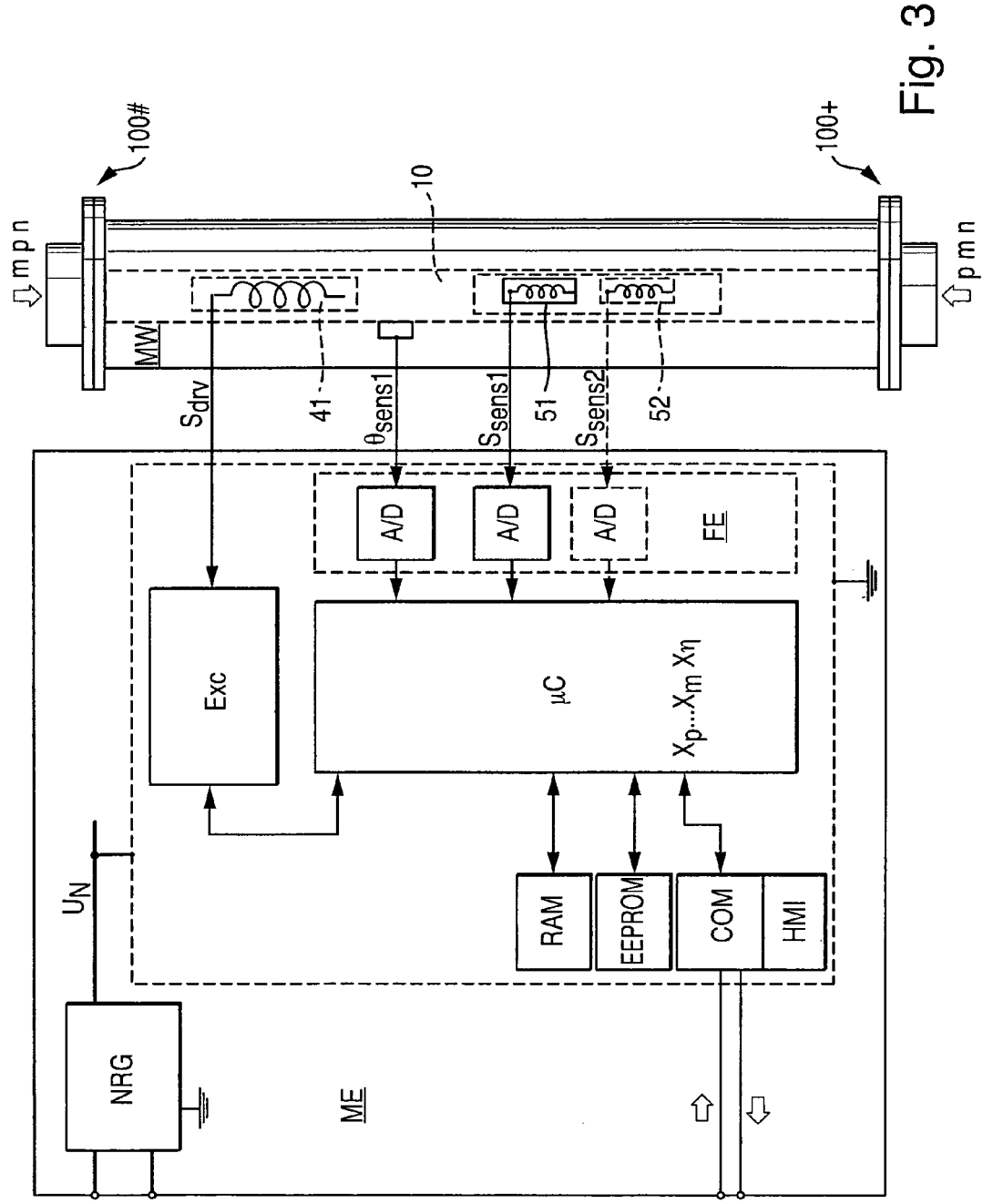
FIG. 3 shows schematically in the manner of a block diagram, a measuring system of FIG. 1 having an electronics and a measuring transducer connected thereto.

FIGS. 1, 2 and 3 show measuring systems schematically, by way of example, especially measuring systems suitable for application in industrial measuring—and automation technology. Such measuring systems serve to measure a density $\rho$ of a flowable fluid FL, for example, thus a liquid, or a gas, guidable in a line, such as, for instance, a pipeline or a flume, or containable in a container, such as, for instance, a tank, and thus to produce sequential measured values $X_\rho$ representing said density as a function of time. The measuring system is implemented here, in each case, as an inline measuring device, namely a measuring system insertable into the course of a pipeline (not shown). The measuring system can accordingly be, for example, a Coriolis, mass flow/density measuring device for measuring, supplementally to density $\rho$, also mass flow rate m of flowing fluids being measured and/or a density/viscosity measuring device for measuring, supplementally to density, also viscosity $\eta$ of flowing fluids.

For registering the density, the measuring system comprises a measuring transducer MT—here a measuring transducer insertable into the course of a pipeline (not shown). During operation, the fluid to be measured flows through the measuring transducer. Measuring transducer MT includes an oscillatably held, vibratory body 10, especially one of metal and—as directly evident from the combination of FIGS. 1, 2 and 3—is electrically connected to a measuring electronics ME accommodated in an electronics housing 200 and lastly delivering the density, measured values $X_\rho$. The vibratory body 10 has a plurality of eigenfrequencies, of which each is determined decisively by the material, respectively modulus of elasticity, as well as by the mechanical construction, respectively the actual installed situation, of the vibratory body.

Figure 4:
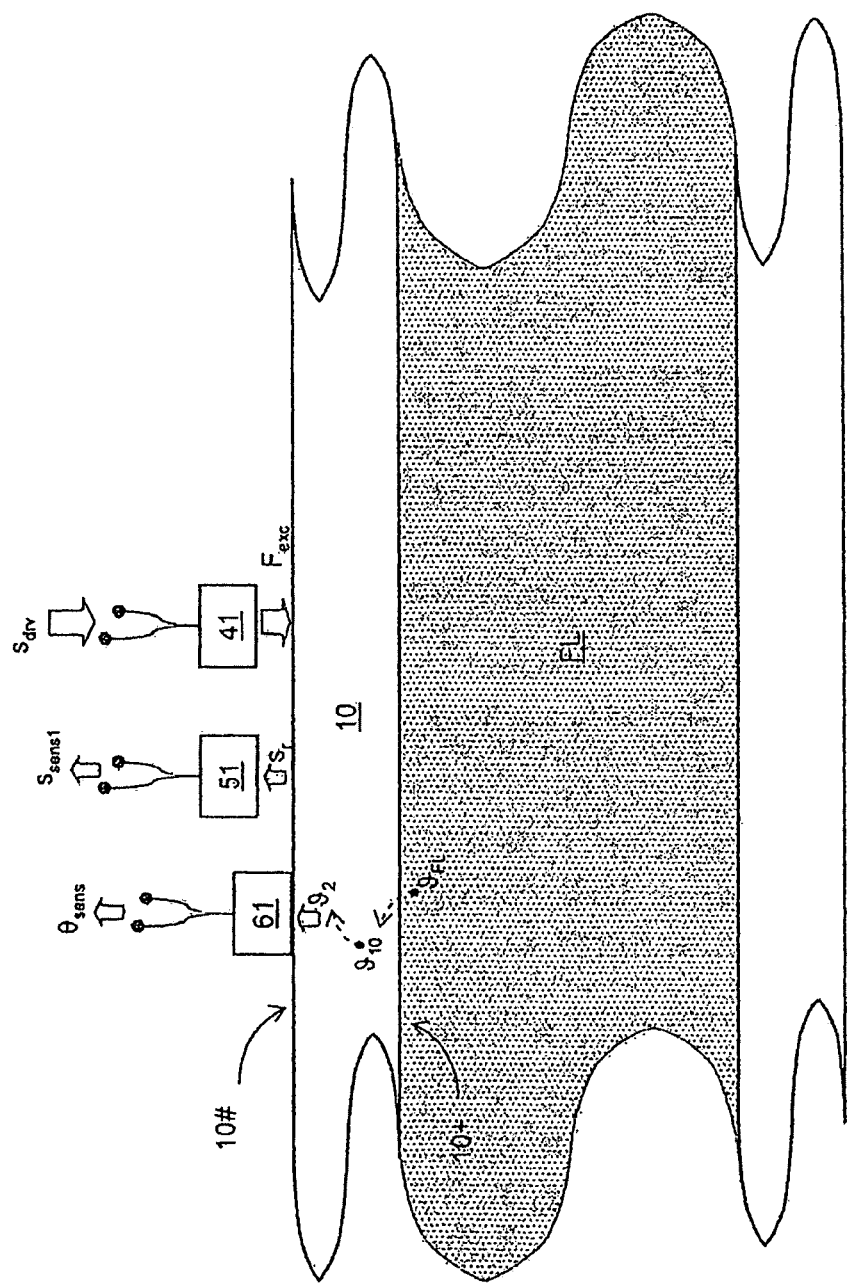
FIG. 4 shows schematically, a sketch of the principles of a measuring arrangement suitable for a measuring system according to FIG. 1, or a measuring transducer according to FIGS. 2 and 3, comprising a vibratory body, an oscillation exciter, an oscillation sensor and a temperature sensor.

The vibratory body 10 is, as schematically presented in FIG. 4, adapted, during operation, to be contacted, at least on a first surface 10+, by the fluid FL to be measured and simultaneously to be excited actively to execute mechanical oscillations, and, indeed, in such a manner that the vibratory body contacted by fluid 10 executes, at least partially, resonant oscillations $o_r$, namely, mechanical oscillations with a resonant frequency $f_r$, which—besides depending on one of the eigenfrequencies—also depend on the density $\rho$ of the fluid contacting the first surface of the vibratory body and can consequently serve as a measure for said density. Moreover, the resonant frequency $f_r$ is, as is known, additionally determined also by a fluid temperature $\theta_{FL}$, namely a temperature of the fluid contacting the first surface, since the eigenfrequencies of the vibratory body, not least of all because of a temperature dependence of a modulus of elasticity of the vibratory body, as well as also a temperature dependent, volume expansion, is influenced decisively also by a temperature $\theta_{10}$, especially an average temperature, of the vibratory body, namely a temperature of the vibratory body dependent on the fluid temperature $\theta_{FL}$.

Based on these mechanical oscillations of the vibratory body 10, the measuring transducer generates, furthermore: At least one oscillation measurement signal $s_{sens1}$ dependent on density, namely having at least one signal component with a signal frequency corresponding to the resonant frequency $f_r$, and representing, consequently, vibrations of the vibratory body 10; as well as at least one temperature measurement signal $\theta_{sens}$ serving for compensating for the influence of temperature of the vibratory body $\theta_{10}$ on the resonant frequency $f_r$, consequently on the oscillation measurement signal $s_{sens1}$. The signal $\theta_{sens}$ corresponds to, in any event, at least approximately represents, a time curve of the temperature $\theta_{10}$ of the vibratory body.

The measuring electronics ME includes, as schematically presented in FIG. 3, consequently, furthermore, a driver-circuit Exc serving for activating the measuring transducer as well as a measuring- and evaluating-circuit μC serving for processing the at least one oscillation measurement signal $s_{sens1}$ of the measuring transducer MT and formed, for example, by means of at least one microprocessor and/or by means of a digital signal processor (DSP). Measuring- and evaluating-circuit μC applies the at least one oscillation measurement signal $s_{sens1}$ to produce the density, measured values, which can, for example, also be in the form of digital values.

The density-measured values generated by means of the electronics ME can, for example, be displayed on-site. For visualizing, on-site, measured values produced internally in the measuring device and/or, in given cases, measuring device internally generated, system status reports, such as, for instance, an error report or an alarm, the measuring device can, as also indicated in FIG. 3, have, for example, a display—and servicing element HMI, which is in communication with the electronics and is, in given cases, also portable. Examples of the display—and servicing element HMI include, for instance, an LCD-, OLED- or TFT display placed in the electronics housing behind a window provided correspondingly therein, as well as a corresponding input keypad and/or a touch screen. In advantageous manner, the, for example, also remotely parameterable, electronics can, furthermore, be so designed that it can, during operation of the measuring device, exchange with a superordinated electronic data processing system, for example, a programmable logic controller (PLC), a personal computer and/or a work station, via a data transmission system, for example, a fieldbus system and/or wirelessly per radio, measuring—and/or other operating data, such as, for instance, current measuring—and/or system diagnosis values or tuning values serving for control of the measuring device. Furthermore, the electronics ME can be so designed that it can be fed by an external energy supply, for example, also via the aforementioned fieldbus system. For the case, in which the measuring device is to be coupled to a fieldbus—or other communication system, the electronics ME, for example, also an on-site and/or via communication system (re-)programmable, electronics ME, can have, additionally, a corresponding communication-interface for data communication, e.g. for sending measuring—and/or operating data, thus, the measured values representing the at least one measured variable, to the already mentioned, programmable logic controller or to a superordinated process control system and/or for receiving settings data for the measuring device. Particularly for the case, in which the measuring device is to be coupled to a fieldbus—or other communication system, the electronics ME includes, consequently, furthermore, a communication interface COM embodied for data communication according to one of the relevant industry standards. Moreover, the electronics ME can have, for example, an internal energy supply circuit ESC, which, during operation, is fed via the aforementioned fieldbus system by an external energy supply provided in the aforementioned data processing system. In such case, the electronics can, furthermore, be so embodied e.g. that it is electrically connectable with the external electronic data processing system by means of a two-wire connection 2L configured, for example, as a 4-20 mA-current loop, and thereby be supplied with electrical energy as well as be able to transmit measured values to the data processing system; the measuring device can, however, for example, also be embodied as a so-called four-conductor-measuring device, in the case of which the internal energy supply circuit ESC of the electronics ME is connected by means of a first pair of lines with an external energy supply and the internal communication circuit COM of the electronics ME by means of a second pair lines with an external data processing circuit or an external data transmission system.

The measuring electronics ME is, furthermore, in the example of an embodiment shown here, accommodated in a corresponding electronics housing 200, especially one impact—and/or also explosion resistantly and/or hermetically sealedly formed and/or modularly built up. Electronics housing 200 can, for example, be arranged removed from the measuring transducer, or, as shown in FIG. 1, be affixed directly on the measuring transducer MT, for example, externally on the transducer housing 100, in order to form a single, compact device. In the case of the example of an embodiment shown here, there is, consequently, placed on the transducer housing 100, furthermore, a necklike transition piece serving for holding the electronics housing 200. Arranged within the transition piece can be, furthermore, a hermetically and/or pressure resistantly sealed duct, for example, sealed by means of glass and/or plastic potting compound, for electrical connecting lines between electrical components of the measuring transducer MT, here, for example, thus the oscillation exciter, or the oscillation sensor, and the electronics ME.

For active exciting of vibrations of the vibratory body, especially also the resonant oscillations required for measuring density, the measuring transducer comprises, furthermore, at least one electro-mechanical oscillation exciter 41 in actuating connection with the vibratory body—, for example, an electrodynamic oscillation exciter 41, namely formed by means of an armature extending movably in a solenoidal coil. Said oscillation exciter 41 is, as schematically presented in FIG. 2, respectively FIG. 4, respectively directly evident from their combination, arranged at a second surface 10# facing away from the first surface 10+ of the vibratory body 10— namely that surface not contacted during operation by the fluid to be measured—and serves, in such case, especially, to convert an electrical excitation power $P_{exc}$ fed from the driver circuit Exc of the electronics ME by means of at least one electrical driver signal $s_{drv}$ into, e.g. pulsating or harmonic, namely essentially sinusoidal, exciter forces $F_{exc}$, which act correspondingly on the vibratory body 10 and, thus, actively excite the desired resonant oscillations. For example, the at least one driver signal $s_{drv}$ can have simultaneously also a plurality of sinusoidal signal components with signal frequencies differing from one another, of which one—, for instance, one at least at times dominating as regards signal power—signal component has a signal frequency corresponding to the resonant frequency $f_r$ required for measuring density. The exciter forces $F_{exc}$ generated by converting electrical excitation power $P_{exc}$ fed into the oscillation exciter can, in such case, in manner known, per se, to those skilled in the art, be correspondingly tuned by means of the driver circuit Exc provided in the electronics ME, for instance, by means of electrical current- and/or voltage-controllers implemented in the driver circuit, controlling an amplitude (electrical current level) of an electrical current of the driver signal and/or an amplitude (voltage level) of a voltage of the driver signal as regards their magnitude, and e.g. by means of a phase control loop (PLL—phase locked loop) likewise provided in the driver circuit Exc, as regards their instantaneous frequency or, in the case of multifrequency excitation, as regards their instantaneous frequencies, compare, for this, for example, also U.S. Pat. No. 4,801,897 or U.S. Pat. No. 6,311,136. The construction and application of the aforementioned phase control loop for the active exciting of vibratory bodies of the type being discussed to an instantaneous resonant frequency is described at length e.g. in U.S. Pat. No. 4,801,897. Of course, also other driver circuits known, per se, to those skilled in the art to be suitable for tuning the exciter energy $E_{exc}$ can be used, for example, also those set forth in the initially mentioned state of the art, for instance, the initially mentioned U.S. Pat. No. 4,777,833, U.S. Pat. No. 4,801,897, U.S. Pat. No. 4,879,911, U.S. Pat. No. 5,009,109, U.S. Pat. No. 5,024,104, U.S. Pat. No. 5,050,439, U.S. Pat. No. 5,804,741, U.S. Pat. No. 5,869,770, U.S. Pat. No. 6,073,495, or U.S. Pat. No. 6,311,136. Furthermore, as regards an application of such driver circuits, reference is made to the electronics provided with measurement transmitters of the sensor series "PROMASS 83", as available from the assignee, for example, in connection with measuring transducers serving also for measuring density in the sensor series "PROMASS E", "PROMASS F", "PROMASS H", "PROMASS I", "PROMASS P", "PROMASS S", or "PROMASS X". Their driver circuit is, for example, in each case, so executed that resonant oscillations are controlled to a largely constant amplitude, consequently also independent of the density ρ, or also the viscosity η, of the respective fluid to be measured.

For registering vibrations of the vibratory body 10, not least of all also the resonant oscillations $o_r$ actively excited by means of the at least one oscillation exciter 41, as well as for transducing said registered vibrations into the at least one oscillation measurement signal $s_{sens1}$, the measuring transducer MT includes, furthermore, at least a first oscillation sensor 51, for example, an electrodynamic sensor,—here one spaced from the at least one oscillation exciter 41—arranged on the second surface 10# of the vibratory body 10. Oscillation sensor 51 lastly delivers the oscillation measurement signal $s_{sens1}$ representing vibrations of the vibratory body, for example, in the form of an electrical (alternating-)voltage corresponding to the oscillations with an amplitude (voltage level) dependent on an instantaneous amplitude of the oscillations of the vibratory body and a frequency corresponding to that of the resonant frequency $f_r$. Moreover, the measuring transducer includes additionally at least one temperature sensor 61 thermally coupled with the vibratory body via its second surface 10#, for example, adhered thereon, for producing the mentioned temperature measurement signal $\theta_{sens}$.

Figure 5:
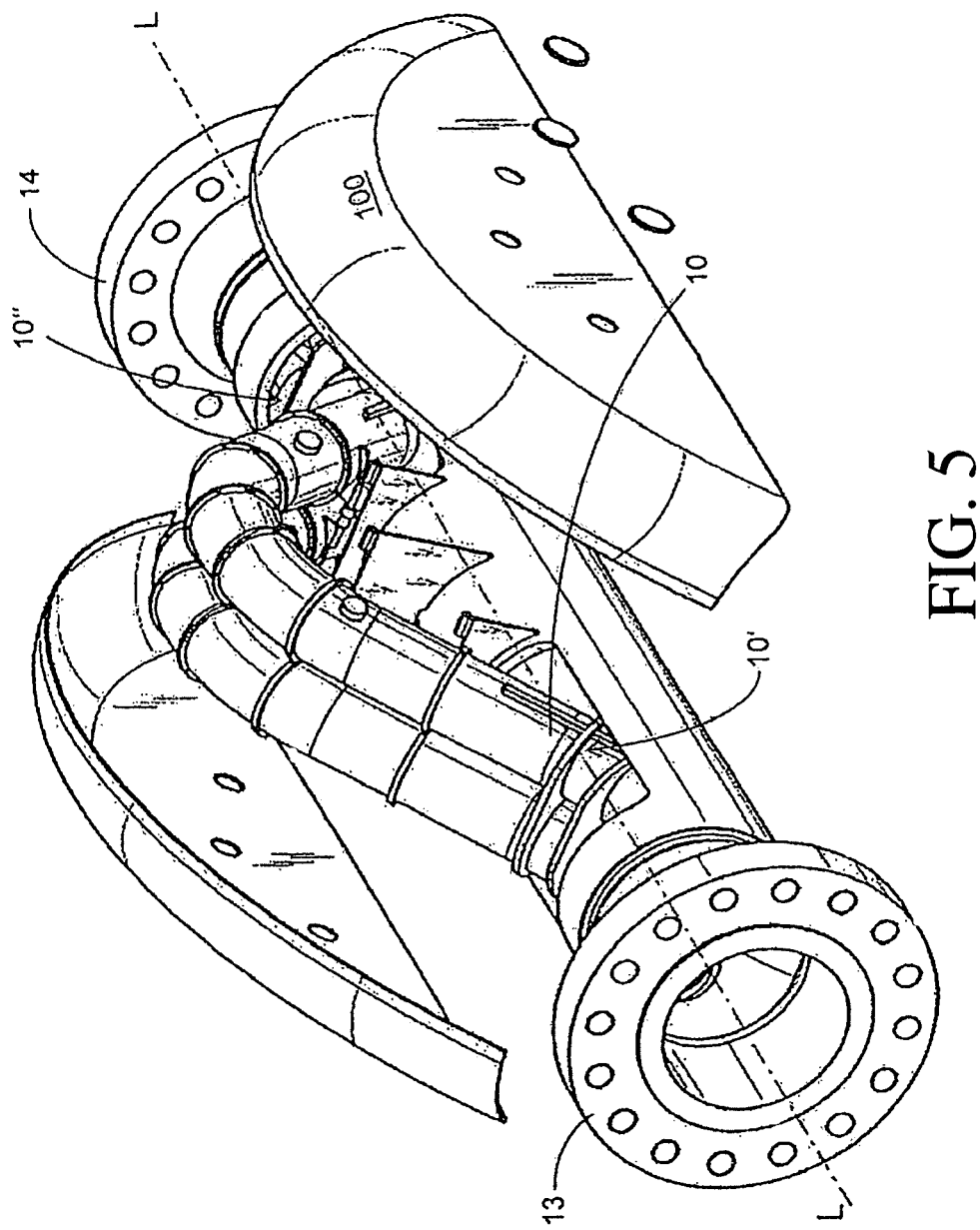
FIG. 5 shows in exploded view, a variant of a measuring transducer, especially a measuring transducer suitable for a measuring system according to FIG. 1, respectively FIG. 2, having a vibratory body formed by means of a measuring tube.

As already mentioned and also schematically presented in FIG. 2, respectively 5, vibratory body 10 can be formed, for example, by means of a measuring tube flowed through during operation by the fluid FL. The measuring tube is accommodated in a measuring transducer housing 100 and held oscillatably therein. The measuring tube has a lumen surrounded by a tube wall, especially one of metal, and extends with a desired oscillatory length between an inlet-side, first measuring tube end 10' and an outlet-side, second measuring tube end 10". The measuring system can accordingly be embodied, for example, also as a Coriolis, mass flow/density measuring device measuring, supplementally to density, also a mass flow of the fluid flowing FL and/or as a viscosity/density measuring device measuring supplementally to density also a viscosity of the fluid. The measuring tube 11, consequently the vibratory body formed therewith, is adapted, in such case, to be flowed through by the fluid to be measured, consequently to carry the volume portion of the fluid to be measured, after it has been allowed to flow into the lumen, wherein the first surface of the vibratory body contacting the fluid is formed by an inner surface of the tube wall facing the lumen and contacted by the fluid and the non fluid contacting, second surface of the vibratory body is formed by an outer surface of the tube wall. The resonant oscillations serving for measuring density can, in such case, for example, be such that the measuring tube serving as vibratory body is caused to vibrate over its entire desired oscillatory length, for example, in a bending oscillation mode, in which the at least one measuring tube deflects about an oscillation axis imaginarily connecting the two measuring tube ends 10', 10" with one another and extending essentially parallel to an imaginary longitudinal axis L of the measuring transducer, in the manner of a unilaterally clamped cantilever, and, in such case, is deformed oscillatingly, repeatedly, elastically about a static resting position. The desired oscillatory length corresponds, in such case, virtually to a length of a middle, or also centroidal, axis (connecting line through the centers of gravity of all cross sectional areas of the measuring tube) extending within the lumen—in the case of a curved measuring tube, thus, a straightened length of the measuring tube. The measuring transducer resembles, in its mechanical construction, as well as also its principle of action, the measuring transducers proposed in U.S. Pat. No. 7,360,451 or U.S. Pat. No. 6,666,098, or also those available from the assignee under the marks "PROMASS H", "PROMASS P" or "PROMASS S" for measuring both density as well as also mass flow of flowing fluids. For implementing the invention, however, also other measuring transducers with vibratory bodies can serve, in the case of measuring transducers with a measuring tube as vibratory body, thus, also such with straight and/or greater than one measuring tube, for example, thus four or, as shown in FIG. 5, two measuring tubes or also such comparable in the initially mentioned US-A 2010/0236338, US-A 2010/0242623, US-A 2010/0242624, U.S. Pat. No. 5,602,345, U.S. Pat. No. 5,731,527, U.S. Pat. No. 5,796,011, U.S. Pat. No. 6,006,609, U.S. Pat. No. 6,513,393, U.S. Pat. No. 6,840,109, U.S. Pat. No. 6,920,798 or U.S. Pat. No. 7,017,424, or, for example, also the measuring transducers available from the assignee under the marks "PROMASS I", "PROMASS M", "PROMASS E", "PROMASS F", or "PROMASS X" for measuring mass flow as well as also density of flowing fluids. In accordance therewith, the measuring transducer can, for example, also be a single straight measuring tube or have at least two measuring tubes, each serving as a vibratory body, for example, mechanically coupled with one another by means of an inlet-side flow divider and an outlet-side flow divider, in given cases, supplementally also by means of in- and outlet-side coupling elements, and/or equally constructed measuring tubes and/or curved ones and/or extending parallel to one another, for conveying the fluid to be measured. During operation, the at least two measuring tubes vibrate opposite—equally to one another, at least at times, for producing the oscillation measurement signals, for instance, with equal frequency at a shared oscillation frequency. Particularly for the case, in which the vibratory body is formed by means of a straight measuring tube, the resonant oscillations $o_r$ can be, for example, also in the form of torsional oscillations or radial oscillations about an oscillation axis parallel to, in given cases, even coincident with, the mentioned longitudinal axis of the measuring transducer.

For the typical case for such a measuring transducer with measuring tube serving as vibratory body, when said measuring transducer MT is to be assembled releasably with the process line, for example, a process line in the form of a metal pipeline, there are provided, as indicated in FIG. 1, 2, or 5, or as directly evident from their combination, on the inlet side (100+) of the measuring transducer, a first connecting flange 13 for connection to a line segment of the process line supplying fluid to the measuring transducer and, on the outlet side (100#), a second connecting flange 14 for a line segment of the process line removing fluid from the measuring transducer. The connecting flanges 13, 14 can, in such case, as quite usual in the case of measuring transducers of the described type, also be integrated terminally in the measuring transducer housing 100, consequently form an inlet-side measuring transducer end 100+, respectively an outlet-side measuring transducer end 100#. In the case of its application in a Coriolis, mass flow measuring device, the measuring transducer, according to an additional embodiment of the invention, includes, furthermore, a second oscillation sensor 52 spaced from the first oscillation sensor 51 in the flow direction, wherein the first oscillation sensor is placed, for example, on the inlet side of the measuring tube serving as vibratory body, while the second oscillation sensor is arranged downstream from the first oscillation sensor, on the outlet side of the measuring tube.

Instead of a measuring transducer with a measuring tube serving as vibratory body, or a measuring system formed therewith, for example, thus implementable as a Coriolis, mass flow-/density measuring device, the density can, however, also be measured by means of some other electro-mechanical oscillatory system serving as vibratory body and bringable in contact with the fluid to be measured. Serving for implementing the invention can be, for example, also such density measuring systems, in the case of which the vibratory body is adapted, for the purpose of registering the density, to be at least partially immersed in, or flowed on by, the fluid to be measured. In accordance therewith, the measuring system can, for example, thus also be a so-called fill level limit switch with integrated density measurement having at least one, for example, paddle shaped appendage and/or internally hollow, oscillatory rod, for example, thus according to the initially mentioned U.S. Pat. No. 6,845,663, so that the vibratory body can have an oscillatably held membrane, in such a manner that the first surface of the vibratory body contacting the fluid is formed by means of a first membrane surface and the non fluid contacting, second surface by a second membrane surface lying opposite the first membrane surface, or the vibratory body can further have a paddle affixed on the first membrane surface, in order that the paddle can protrude into the fluid. Furthermore, the measuring system can be, for example, a Coriolis, mass flow-/density measuring device with a vibratory body in the form of a hollow body, which can be inserted through a wall of a pipeline, such as, for instance, according to the initially mentioned EP-A 564 682, such as in the form of an at least unilaterally sealed, internally hollow cylinder.

The at least one oscillation measurement signal $s_{sens1}$ generated by the measuring transducer as well as also the temperature measurement signal $\theta_{sens}$ are, as is schematically presented FIGS. 2 and 3, or as directly evident from their combination, fed to the electronics ME, in order there, first of all, to be preprocessed, especially preamplified, filtered and digitized by means of an input circuit FI of the electronics connected in front of the therein provided, actual measuring—and evaluating circuit µC. After this preprocessing, evaluation follows, namely, the signal is at least converted into the at least one measured value of density $X_\rho$, or other, later, measured values of density; this is done, in given cases, also taking into consideration electrical excitation power fed into the exciter mechanism by means of the at least one driver signal, there to be converted into excitation force. Particularly for the purpose of generating the measured value of density $X_\rho$, the measuring—and evaluating circuit µC ascertains, based on the oscillation measurement signal $s_{sens1}$, recurringly a measured value $X_f$ of frequency serving as measure for a resonant frequency, consequently representing said resonant frequency and forming a basis for determining the current measured value $X_\rho$ of density, as well as, based on the temperature measurement signal $\theta_{sens}$, at times, also a measured value $X_\theta$ of temperature, which serves as a measure for the one temperature of the vibratory body that determines the eigenfrequency forming a basis for determining the current measured value of density $X_\rho$, consequently representing said temperature of the vibratory body. With the measured value $X_f$ of frequency and the measured value $X_\theta$ of temperature, the measured value $X_\rho$ of density can be ascertained in manner, per se, familiar to those skilled in the art, for instance, based on the known approximation formula $$X_\rho \sim K \cdot \frac{1 + X_\theta}{X_f^2} + \dots ,$$

thus by dividing the measured value $X_\theta$ of temperature by a squared measured value $X_f$ of frequency.

In the case of application in a Coriolis, mass flow-measuring device, the electronics ME serves, furthermore, also, with application of the oscillation measurement signals generated by the measuring transducer, namely based on a phase difference detected between the oscillation measurement signals $s_{sens1}$, $S_{sesn2}$ of the first and second oscillation sensors 51, 52, as caused by Coriolis forces in the flowing fluid, recurringly to ascertain a mass flow measured value $X_m$, which represents a mass flow rate, m, to be measured for fluid guided through the measuring transducer. Alternatively thereto or in supplementation thereof, the measuring—and evaluating circuit can, as quite usual in the case of measuring systems formed by means of a vibratory body for measuring density, in given cases, also be applied, based on the fed-in electrical excitation power $P_{exc}$ as well as the at least one oscillation measurement signal $s_{sens1}$, to ascertain a viscosity measured value $X_\eta$ representing a viscosity $\eta$ of the fluid; compare, for this, also the initially mentioned U.S. Pat. No. 7,284,449, U.S. Pat. No. 7,017,424, U.S. Pat. No. 6,910,366, U.S. Pat. No. 6,840,109, U.S. Pat. No. 5,576,500 or U.S. Pat. No. 6,651,513.

The program code for such evaluating programs serving for generating measured values, not least of all also the density, measured values, or control programs serving for operating the measuring transducer can be stored e.g. persistently in a non-volatile data memory EEPROM of the electronics and, upon start up of the electronics, loaded into a volatile data memory RAM, e.g. one integrated into the processor. Equally, measured values generated by means of the electronics ME during operation can be loaded into such a (in given cases, also the same) volatile, or into such a non-volatile, data memory and correspondingly held for later, further processing.

As already mentioned, methods for ascertaining the density of fluids based on resonant oscillations of a vibratory body can, at times, exhibit considerable measuring inaccuracies, this, especially being the case during a transition time period directly following on a change of the fluid FL, during which time period the measuring system transfers from a steady state occupied before the fluid change into a changed state determined by the new fluid. Further investigations on measuring systems of the type being discussed have led to the result that such measuring inaccuracies can be explained partially by the fact that such a fluid change can, on the one hand, regularly also be accompanied with a significant change of the fluid temperature $\theta_{FL}$ effective for the measuring, on the other hand, however, exactly this change of the fluid temperature, or the effect thereof on the entire measuring system, has so far been looked upon as negligible, or completely overlooked, in any event, however, not sufficiently taken into consideration, in the functions $f_r^2 = f(1/\rho)$, or $f_r^2 = f(\theta_{10})$, $\theta_{sens} \sim \theta_{10}$ holding actually only for steady state conditions. The vibratory body 10 has, namely, both a certain heat capacity, $C_{10}$, as well as also a specific thermal conductivity $\lambda_{10}$—amounting usually to greater than 5 W K$^{-1}$ m$^{-1}$—and accordingly a thereon dependent, effective thermal conductance, $\Lambda_{10}$, consequently a certain thermal inertia, for heat transfer from the first surface 10+ of the vibratory body, naturally having the fluid temperature, to its second surface 10#. Thus, the temperature of the vibratory body $\theta_{10}$ changes not only directly after a change of the fluid temperature initiated, for example, by a fluid change, but, also as a result of its thermal inertia dependent on the heat capacity, $C_{10}$ and the thermal conductance, $\Lambda_{10}$, also over a certain amount of time much longer than a measuring cycle time required for ascertaining a measured value of density $X_\rho$. Associated therewith, however, also the temperature $\theta_2 \rightarrow \theta_{sens}$ actually registered by the temperature sensor 61 on the second surface 10# of the vibratory body 10 deviates during the transition time period always from the temperature of the vibratory body $\theta_{10}$ actually effective for the oscillation characteristics, and, indeed, in an amount changing as a function of time. Alone already because of this, thus the temperature measurement signal $\theta_{sens}$ can follow, however time delayed, a change of the temperature of the vibratory body $\theta_{10}$ from a beginning first temperature value $\Theta_{10,t1}$ to a second temperature value $\Theta_{10,t2}$ (for example, thus a change resulting from a change of the temperature of the fluid contacting the vibratory body on its first surface 10+ and/or a fluid change); consequently, the temperature measurement signal $\theta_{sens}$ corresponds to said second temperature value, only time delayed, however, without that this, or a therefrom resulting dynamic measuring error in the case of ascertaining the density, has so far been correspondingly taken into consideration. For example, thus the temperature $\theta_2 \rightarrow \theta_{sens}$ on the second surface 10# of the vibratory body 10, thus the temperature signal $\theta_{sens, can}$, during a transition time period of the aforementioned type, exhibit a time curve, which approximately corresponds to that shown in FIG. 6a.

As another cause for measuring inaccuracies of the aforementioned type, there is also an inherent thermal inertia of the temperature sensor, which yet further increases the dynamic measuring errors of conventional measuring systems of the type being discussed.

Figure 6A:
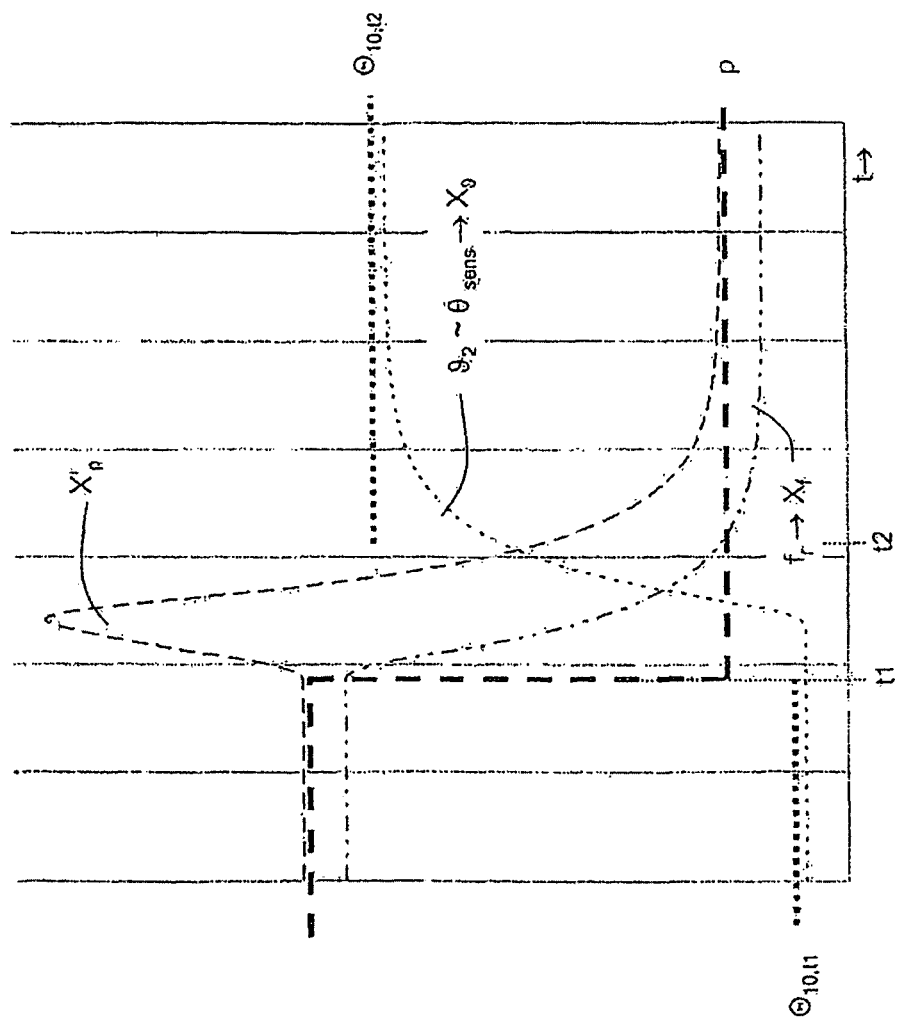
FIG. 6a shows time curves ascertained by means of a measuring transducer according to FIGS. 2, 3, and/or 4 of an actual density to be measured, a measured resonant frequency of the vibratory body, an temperature measured on the vibratory body, as well as a measured density derived therefrom in conventional manner.

As a result of such temperature $\theta_{10}$ of the vibratory body continually changing during the transition time period, yet so far, however, not correctly, or not at all, considered in the ascertaining, there has to change correspondingly also the oscillation characteristics of the vibratory body 10, so that, thus, a change of the resonant frequency $f_r$ associated with the fluid change is, as a result, not—as previously—alone to be attributed to the corresponding change of the density, but, instead, additionally also to a thermally related change of the eigenfrequency co-determining the resonant frequency $f_r$ of the vibratory body 10. Furthermore, this means that, during the transition time period for the temperature $\theta_{10}$ of the vibratory body, the resonant frequency ascertained based on the at least one oscillatory signal $s_{sens1}$ in the form of corresponding frequency measured values $X_f$—for which, in FIG. 6a, by way of example, a corresponding time curve containing said transition time period is shown—can, indeed, correspond very exactly to the actual resonant frequency $f_r$, nevertheless, however, therefrom derived density, measured values $X'_\rho$—of which likewise a corresponding time curve is shown in FIG. 6a—can, in the meantime, deviate in considerable measure from the instantaneous density $\rho$, because the temperature $l'_2 \rightarrow \theta_{sens}$ on the second surface 10# of the vibratory body 10 utilized for its ascertaining, consequently the therefrom, in each case, derived, measured values $X_\theta$ of temperature only approximately reflect the actually required temperature of the vibratory body $\theta_{10}$, or a time curve therefrom, as is directly evident from FIG. 6a. As a result of this, the density $X'_\rho$ ascertained in conventional manner for the above-described time curve of measured resonant frequency ($f_R \rightarrow X_f$) and temperature measured ($\theta_2 \rightarrow X_\theta$), namely without corresponding taking into consideration of the dynamic behavior of the temperature measuring chain, can approximately correspond to the curve shown in FIG. 6a, wherein, clearly recognizably, not only a density erroneous in considerable measure is ascertained, but, also, first of all, namely directly after completed fluid change, regretfully even an increasing density is suggested, although it has really decreased from what it was—for instance, as a result of using a fluid, which is only warmer, but otherwise essentially the same.

Taking this into consideration, the measuring system of the invention is, consequently, furthermore, adapted, and the method implemented therewith for measuring the density, furthermore, so embodied, that, in producing the measured value of density $X_\rho$, based on the at least one oscillation measurement signal $s_{sens1}$ as well as the at least one temperature measurement signal $\theta_{sens}$, during a change of the temperature $\theta_{10}$ of the vibratory body—for example, thus a temperature change resulting from a change of the fluid temperature $\theta_{FL}$, or the temperature of the vibratory body 10 on its first surface 10+, upon a replacement of a fluid supplied earlier to the vibratory body with a differently characterized fluid FL—a discrepancy $\text{Err}'_\theta = \theta_{sens} - \theta_{10}$ occurring during the producing of said measured value of density between the time curve of the temperature of the vibratory body and the temperature measurement signal is taken into consideration. In the simplest case, the taking into consideration of the discrepancy can be that its occurrence is detected and signaled, for example, in the form of a report indicated on-site, and/or is documented by storing in the data memory, in given cases, accompanied by a time stamp.

In an additional embodiment of the invention, it is, furthermore, provided that the discrepancy, which usually gets smaller with time, and is, consequently, time dependent, is taken into consideration already in the ascertaining of the measured value $X_f$ of frequency and/or the measured value $X_\theta$ of temperature, for example, by calculation by means of the measuring- and evaluating-circuit μC and/or by suitably conditioning the temperature measurement signal $\theta_{sens}$ by means of a signal filter correspondingly adapted as regards its transfer behavior, and, indeed, in such a manner that the thermal inertia of the vibratory body and/or of the temperature sensor, consequently said discrepancy, is at least partially compensated in the case of ascertaining the measured value of density.

Fundamentally, there are essentially thus at least three approaches computationally, by suitable signal processing of the at least one oscillation measurement signal as well as the at least one temperature measurement signal, to compensate the aforementioned discrepancy existing between the time curve of the temperature of the vibratory body and the temperature measurement signal and resulting from the thermal inertia of the measuring chain comprising the vibratory body as well as the temperature sensor contacting such and serving for ascertaining the temperature of the vibratory body. These approaches include a corresponding delaying (namely making movement of the resonant frequency toward a steady end value slower than it would otherwise be) of a time curve of the resonant frequency of the vibratory body (FIG. 6b) ascertainable based on signal processing of the oscillation measurement signal, or by a corresponding accelerating (namely, making temperature move faster toward a steady end value than the temperature registered on the second surface 10# of the vibratory body 10) of a time curve of the temperature on the second surface of the vibratory body 10 ascertainable based on signal processing of the temperature measurement signal (FIG. 6c) or by a corresponding combination of said signal processing delaying of the time curve of the resonant frequency and said signal processing accelerating of the time curve of the temperature on the second surface of the vibratory body.

Figure 6B:
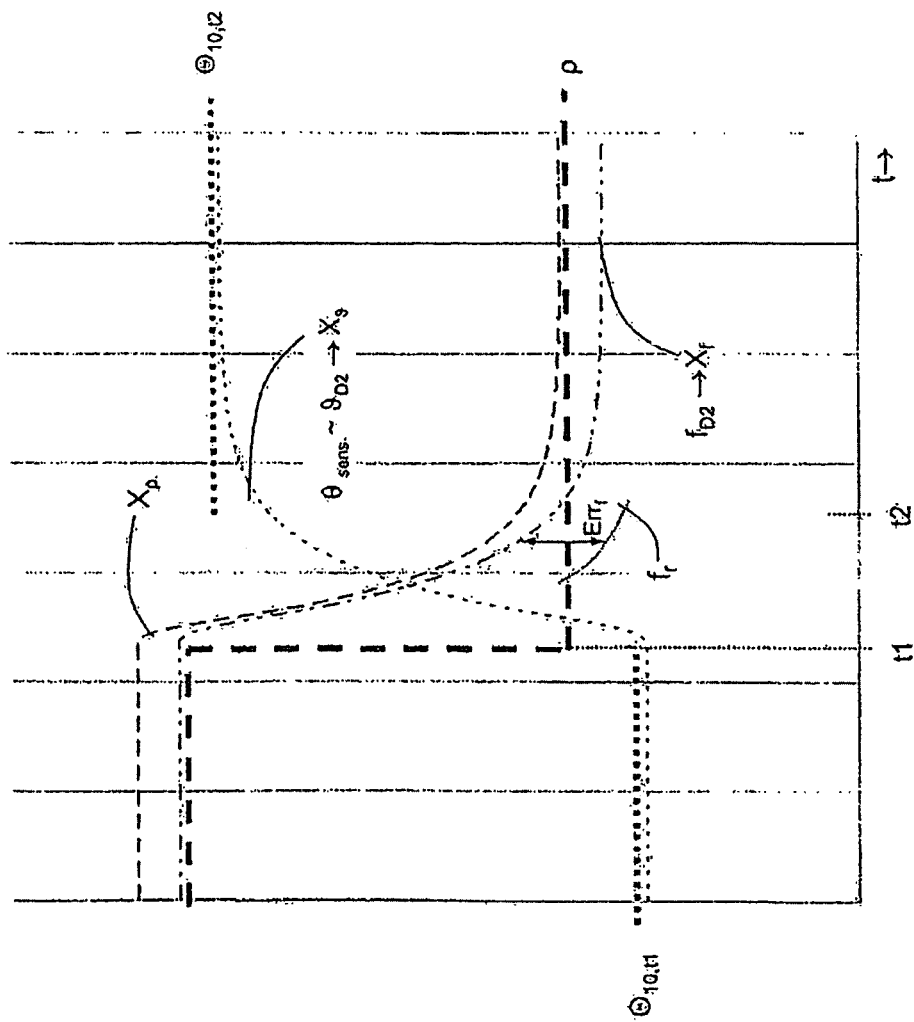
FIGS. 6b, and 6c show time curves ascertained by means of a measuring transducer according to FIGS. 2, 3, and/or 4 of an actual density to be measured, a corrected resonant frequency of the vibratory body, respectively a corrected temperature of the vibratory body as well as a measured density derived therefrom.

In an additional embodiment of the invention, consequently, the measuring- and evaluating-circuit μC, first of all, produces a sampled sequence $f_{D1}$ of frequency, namely a sequence of digital frequency values $X_{f1}$ ascertained at different points in time, for example at equidistant points in time based on the at least one oscillation measurement signal $s_{sens1}$ and approximating, namely at least approximately corresponding to $(f_{D1} \sim f_r)$, a time curve of the resonant frequency $f_r$ of the vibratory body. Furthermore, it is provided according to a variant of the invention further developing this embodiment that the sampled sequence $f_{D1}$ of frequency is applied for producing a delayed sampled sequence $f_{D2}$ of frequency, namely a sequence of digital frequency values $X_{f2}$ ascertained at different points in time, for example, at equidistant points in time $t_n = n \cdot T_s$, consequently with a clocking rate, especially a constant, clocking rate, $f_s = 1/(t_{n+1} - t_n) = 1/T_s$, based on the sampled sequence $f_{D1}$ of frequency, and—as schematically presented in FIG. 6b—approximating the time curve of the resonant frequency $f_r$ of the vibratory body in such a manner that said delayed sampled sequence $f_{D2}$ of frequency approaches an actual time curve $f_r(t)$ of the resonant frequency $f_r$ following on a change of the resonant frequency, for example, a ramp shaped or even, as shown in FIG. 6b, a jump shaped change of the resonant frequency, more slowly than the sampled sequence of frequency $f_D$ (corresponding to the time curve $f_r \rightarrow X_f$ in FIG. 6a). An, in each case, currently (namely, ascertained at the point in time $t_n$) ascertained frequency value $X_{f2}[n]$ of the delayed sampled sequence of frequency $f_{D2}$ serves here, in each case, then also as current measured value of frequency $X_{f2}[n] \rightarrow X_f[n]$. As a result of this, thus a currently ascertained, digital measured value $X_f[n]$ of frequency during a transition time period transient at least as regards the temperature of the vibratory body deviates, for example, as a result of a change of fluid or a change of the fluid temperature, always from the actually, or instantaneously, registered resonant frequency $f_r$ at the point in time $t_n$ by a certain difference amount $\text{Err}_f = X_f[n] - f_r$ becoming smaller as the end of the transition time period is approached, in order ultimately, after reaching again a new steady state of the measuring system determined by the instantaneous fluid temperature and the instantaneous density, to correspond again exactly to the actual resonant frequency $f_r$.

Accordingly serving for generating the delayed sampled sequence $f_{D2}$ of frequency, consequently for generating the therefrom derived frequency measured values $X_f[n]$, can be a digital filter embodied, for example, as an IIR filter (infinite response filter) or also an FIR filter (finite response filter), which has a transfer function $G^*(z) = Z(g[n])$ corresponding to a lowpass filter of first or even higher order. In the case of application of a FIR filter (finite response filter) as digital filter, the transfer function is defined, as is known, by the simple calculational formula $$G^*(z) = Z(g[n]) = \sum_{k=0}^{N} w_k \cdot z^{-k} = \sum_{k=0}^{N} w_k \cdot e^{-j\omega T_s} = \sum_{k=0}^{N} w_k \cdot e^{-j\omega(t_{n+1} - t_n)},$$

wherein, in the case of a digital filter formed as an interpolator corresponding to a pure lowpass filter, all of the filter coefficients $w_k$ have positive sign. In accordance therewith, as in the case of an FIR filter, for the purpose of generating the delayed sampled sequence $f_{D2}$ of frequency, consequently for the purpose of ascertaining a, in each case, current measured value of frequency $X_f[n]$, sequential frequency values of the sampled sequence $f_{D1}$ of frequency are summed with weighting according to the calculational recipe $$X_f[n] \leftarrow X_{f2}[n] = \sum_{k=0}^{N} w_k \cdot X_{f1}[N-k]$$

representing the aforementioned transfer function, consequently the digital filter, in the sampling range. The parameters defining the transfer function, namely the filter coefficients $w_k$, as well as a filter length N corresponding to their number, can, in such case, independently of the type of filter (IIR—, or FIR filter), be so selected, for example, that the therewith established transfer function of the digital filter approaches the dynamic transfer behavior of the measuring chain formed by means of the vibratory body and the temperature sensor, namely its thermal inertia, so that thus a time curve of the delayed sampled sequence $f_{D2}$ of frequency corresponds during a transient transitional period of the above-described type to the time curve of the temperature on the second surface of the vibratory body 10, or to the time curve of the temperature signal representing such.

Figure 6C:
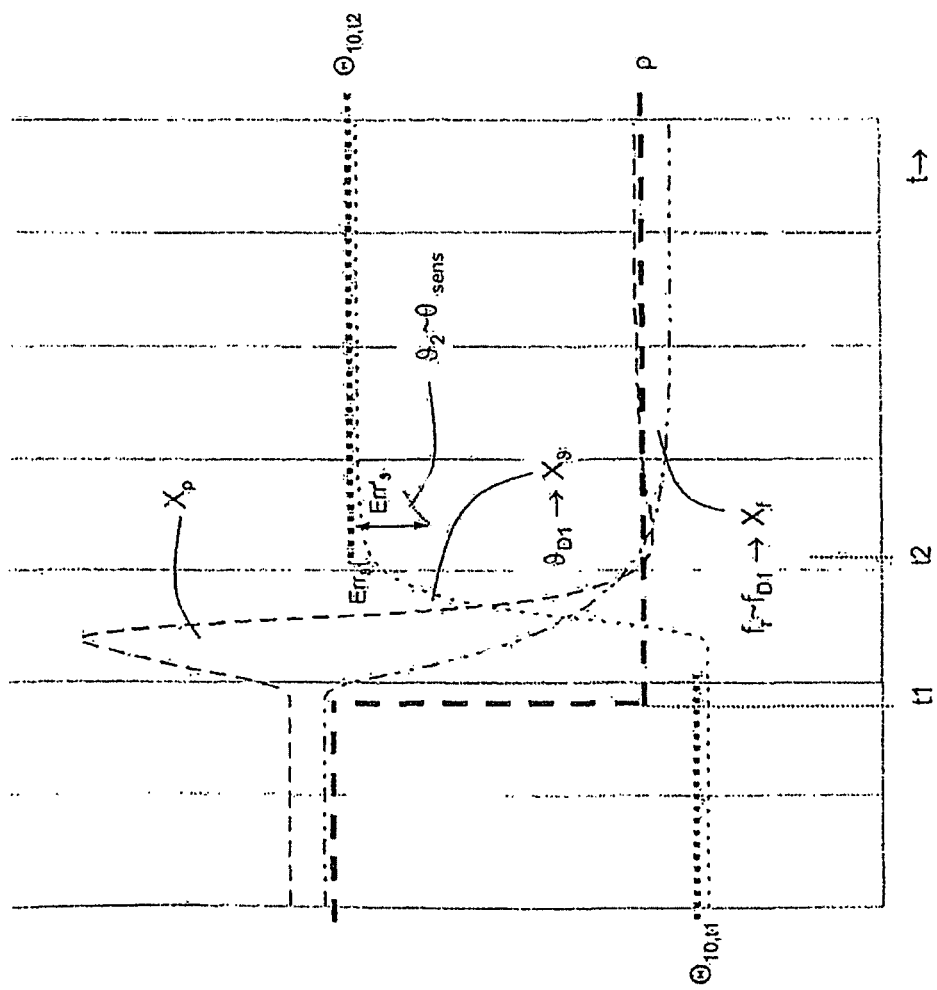

In an additional variant of the invention, not least of all for the purpose of ascertaining the measured value $X_\theta$ of temperature, by means of the measuring- and evaluating-circuit μC, an estimated sequence $\theta_{D1}$ of temperature of the vibratory body, namely a sequence of digital temperature values $X_{\theta 1}$ based on the at least one temperature measurement signal ascertained at different points in time, for example, equidistant points in time $t_m = m \cdot T_{s2}$, consequently with a clocking rate, especially a constant clocking rate $f_{s2} = 1/(t_{m+1} - t_m) = 1/T_{s2}$, is formed to approximate a time curve of the temperature of the vibratory body, in such a manner that said estimated sequence of temperature of the vibratory body—as schematically presented in FIG. 6c, or also evident from a combination of FIGS. 6a and 6c—approaches a time curve of the temperature of the vibratory body following on a change of the temperature on the second surface of the vibratory body—, for instance, a jump-like change and/or a change resulting from a change of the fluid temperature—more quickly than the temperature measurement signal $\theta_{sens}$. A temperature value $X_{\theta 1}[m]$ of the estimated sequence $\theta_{D1}$ of temperature of the vibratory body, in each case, currently ascertained, namely ascertained for the point in time $t_m$, serves here, in each case, then also as current measured value of temperature $X_{\theta 1}[m] \rightarrow X_\theta[m]$. As a result of this, thus a digital measured value $X_{\theta 1}[m]$ of temperature ascertained during a transition time period of the type being discussed deviates currently from the actual temperature $\theta_{10}$ of the vibratory body at the point in time $t_m$ by a difference amount $Err_\theta = X_{\theta 1}[m] - \theta_{10}$, which is at least smaller than an instantaneous deviation between the temperature measurement signal $\theta_{sens}$ delivered at the moment by the temperature sensor and the instantaneous temperature $\theta_{10}$ of the vibratory body corresponding to the instantaneous discrepancy $Err'_\theta$ to be taken into consideration—ideally, however, it is as small as possible.

The estimated sequence of temperature of the vibratory body can be generated, for example, by feeding the temperature measurement signal to an analog signal filter, which has at least one signal transmission path with a high pass-characteristic, where, as regards transfer function, the temperature measurement signal is differentiated, such that the filter is designed as a high pass of first order characterized by one time constant or a high pass of higher order characterized by a number of time constants. The signal filter can, in the simplest case, be formed, for example, by means of correspondingly connected resistors, capacitors and/or coils, consequently by means of a filter network implemented only with passive electrical components or, however, also implemented as an active signal filter having, namely, additionally also operational amplifiers. By suitable trimming of the components defining the signal filter as regards its transfer function, the signal filter can, in such case, be so tuned that it at least partially compensates the mentioned thermal inertia of the measuring chain, which lastly causes the dynamic measuring errors during the transient transition period, namely by taking into consideration also time changes of the temperature measurement signal to deliver a corresponding output signal, which leads the temperature measurement signal, or its time curve, consequently, relative to the actual time curve of the temperature of the vibratory body, at least trails less than the temperature measurement signal. The accordingly equally analog, output signal can thereafter be digitized in conventional manner, namely converted into the—digital—estimated sequence of temperature of the vibratory body. Of course, the estimated sequence of temperature of the vibratory body can e.g., however, also be generated by, first of all, digitizing the temperature measurement signal, consequently ascertaining a sampling sequence, $\theta_{D2}$, of surface temperature, namely a sequence of digital temperature values at different points in time $t_m$ is produced based on the at least one temperature measurement signal, in order to approximate a time curve of the temperature on the second surface of the vibratory body, and thereafter deriving therefrom the estimated sequence of temperature of the vibratory body by processing the sampling sequence of surface temperature by means of a correspondingly adapted digital filter, namely a digital filter differentiating the sampling sequence of surface temperature, in order to obtain the estimated sequence of temperature of the vibratory body. The digital filter can be, for example, a FIR filter with a highpass characteristic, the filter coefficients $w_k$ of which thus have at least two sequential, non-zero, filter coefficients $w_i$, $w_{i+1}$ of different sign.

For additionally improving the accuracy of the density, measured values ascertained by means of the measuring system of the invention, it can be advantageous, furthermore, supplementally to the temperature of the vibratory body, also to register possible mechanical deformations of the vibratory body, for instance, deformations occurring as a result of changing temperature of the vibratory body and/or as a result of forces acting on the vibratory body, or therefrom resulting mechanical stresses within the vibratory body and correspondingly to take such into consideration in the case of calculating the density, measured values. Therefore, the measuring system according to an additional embodiment of the invention includes a strain sensor (not shown) for producing a time curve of a deformation of the vibratory body, namely a deformation measurement signal representing deformation of the vibratory body dependent on the temperature of the vibratory body and/or a force acting on such. The strain sensor, embodied, for example, as strain gages, is mechanically coupled with the vibratory body, namely via its second surface, and can, for example, be affixed, for example, adhered, directly to the vibratory body in the immediate vicinity of the at least one temperature sensor. Based on the at least one deformation measurement signal, for the purpose of taking the registered strain into consideration in generating the at least one measured value of density, this can likewise be digitized, consequently a corresponding sampling sequence of deformation, namely a sequence of digital deformation measurement values ascertained at different points in time can be generated based on the at least one deformation measurement signal, in order to approximate a time curve of the deformation of the vibratory body.

The invention claimed is:

1. A measuring system for ascertaining density of a fluid, said measuring system comprising:
   a measuring transducer including:
     at least one vibratory body, said vibratory body being held oscillatably and adapted to be contacted on a first surface by fluid to be measured in such a manner that said first surface assumes a fluid temperature, namely a temperature of the fluid contacting said first surface, and to be caused to vibrate in such a manner that it executes, at least partially, resonant oscillations, namely mechanical oscillations with a resonant frequency, dependent on the density of the fluid, and said vibratory body exhibiting a specific thermal conductivity, consequently a therefrom dependent, thermal conductivity, effective for heat transfer from said first surface to a non fluid contacting, second surface, and a heat capacity;

at least one oscillation sensor for registering vibrations of said vibratory body and for producing an oscillation measurement signal, which includes at least one signal component with a signal frequency dependent on the density of the fluid; and a temperature sensor thermally coupled with said second surface of said vibratory body for registering a temperature on said second surface of said vibratory body dependent on the fluid temperature, and for producing a temperature measurement signal representing a time curve of a temperature of said vibratory body, namely a temperature dependent on the fluid temperature of said vibratory body, said temperature measurement signal, following a change of the temperature of said vibratory body from a beginning first temperature value, to a second temperature value, only time delayed, so that the temperature measurement signal corresponds consequently to said second temperature value only time delayed;

and said measuring system comprising: an electronics electrically connected with said measuring transducer for processing the oscillation measurement signal and the temperature measurement signal as well as for generating, based on both the oscillation as well as also the temperature measurement signal, a density measured value, representing the density of the fluid, said electronics being adapted, to generate the density measured value taking into consideration an occurrence of a discrepancy between the time curve of the temperature of the vibratory body and the temperature measurement signal wherein: the electronics is adapted to produce a sampled sequence of frequency, namely a sequence of digital frequency values ascertained at different points in time based on the at least one oscillation measurement signal, said sampled sequence approximating a time curve of the resonant frequency of the vibratory body;

the electronics is adapted to apply the sampled sequence of frequency for producing a delayed sampled sequence of frequency, namely a sequence of digital frequency values ascertained at different points in time based on the sampled sequence of frequency, in order to approximate the time curve of the resonant frequency of the vibratory body, in such a manner that said delayed sampled sequence of frequency more slowly approaches a time curve of the resonant frequency following on a change of the resonant frequency;

the electronics is adapted to apply the delayed sampled sequence of frequency for producing a frequency measured value representing the resonant frequency of the vibratory body contacted by the fluid; and the electronics is adapted to apply the frequency measured value for producing the density measured value.

2. The measuring system as claimed in claim 1, wherein:
said vibratory body is adapted to carry fluid, respectively to be flowed through by fluid.

3. The measuring system as claimed in claim 1, wherein:
the change of the temperature results from a change of the temperature of the fluid contacting said vibratory body on its first surface.

4. The measuring system as claimed in claim 1, wherein:
the change of the temperature results from a change of the fluid.

5. The measuring system as claimed in claim 1, wherein:
said discrepancy between the time curve of the temperature of the vibratory body and the temperature measurement signal is time dependent.

6. The measuring system as claimed in claim 1, wherein:
the electronics is adapted to take into consideration said occurrence of the discrepancy between the time curve of the temperature of the vibratory body and the temperature measurement signal in such a manner that said discrepancy is at least partially compensated.

7. The measuring system as claimed in claim 1, wherein:
the vibratory body exhibits a specific thermal conductivity greater than 5 W K−1 m−1.

8. The measuring system as claimed in claim 1, wherein:
the vibratory body is of metal.

9. The measuring system as claimed in claim 1, wherein:
the electronics is adapted to apply the temperature measurement signal for producing a temperature measured value representing the temperature of the vibratory body; and the electronics is adapted to apply both, the frequency measured value as well as also the temperature measured value for producing the density measured value.

10. The measuring system as claimed in claim 1, wherein:
the electronics is adapted to apply the sampled sequence of frequency for producing the frequency measured value.

11. The measuring system as claimed in claim 1, wherein:
the change of the resonant frequency is a jump-like change of the resonant frequency.

12. The measuring system as claimed in claim 1, further comprising:
at least one electro-mechanical oscillation exciter in actuating connection with the vibratory body adapted.

13. The measuring system as claimed in claim 12, wherein:
the measuring electronics includes a driver-circuit serving for activating the measuring transducer; and the electro-mechanical oscillation exciter is adapted to convert an electrical excitation power fed from the driver circuit of the electronics by means of at least one electrical driver signal into exciter forces, which act correspondingly on the vibratory body.

14. The measuring system as claimed in claim 1, wherein the measuring electronics includes a measuring- and evaluating-circuit serving for processing the at least one oscillation measurement signal of the measuring transducer.

15. The measuring system as claimed in claim 14, wherein the measuring- and evaluating-circuit includes at least one of: a microprocessor and a digital signal processor.

16. The measuring system as claimed in claim 1, wherein:
said vibratory body is an oscillatably held measuring tube exhibiting a lumen surrounded by a tube wall.

17. The measuring system as claimed in claim 16, wherein:
said measuring tube is adapted to be immersed in fluid; and
said first surface of said vibratory body contacting the fluid is formed by an outer surface of the tube wall and the non fluid contacting, second surface of said vibratory body by an inner surface of the tube wall facing the lumen.

18. The measuring system as claimed in claim 16, wherein:
said measuring tube is adapted to carry fluid; and
said first surface of said vibratory body contacting the fluid formed by an inner surface of the tube wall facing the lumen and the non fluid contacting, second surface of said vibratory body by an outer surface of the tube wall.

19. The measuring system as claimed in claim 1, wherein:
said vibratory body is adapted to be immersed in fluid, or flowed on by fluid.

20. The measuring system as claimed in claim 19, wherein:
said vibratory body includes an oscillatably held membrane; and
said first surface of said vibratory body contacting the fluid is formed by means of a first membrane surface of said membrane and the non fluid contacting, second surface is formed by means of a second membrane surface of said membrane lying opposite the first membrane surface.

21. The measuring system as claimed in claim 20, wherein:
said vibratory body further comprises a paddle affixed on the first membrane surface for protruding into the fluid.

\* \* \* \* \*